(12) United States Patent
Wardle et al.

(10) Patent No.: US 6,875,182 B2
(45) Date of Patent: Apr. 5, 2005

(54) ELECTROSURGICAL SPECIMEN-COLLECTION SYSTEM

(75) Inventors: John L. Wardle, San Clemente, CA (US); Fred H. Burbank, Laguna Niguel, CA (US); Paul Lubock, Laguna Niguel, CA (US)

(73) Assignee: SenoRx, Inc., Aliso Viejo, CA (US)

( * ) Notice: Subject to any disclaimer, the term of this patent is extended or adjusted under 35 U.S.C. 154(b) by 256 days.

(21) Appl. No.: 10/136,700

(22) Filed: Apr. 30, 2002

(65) Prior Publication Data

US 2002/0120211 A1 Aug. 29, 2002

Related U.S. Application Data

(63) Continuation-in-part of application No. 09/619,867, filed on Jul. 20, 2000, now Pat. No. 6,517,498, which is a continuation of application No. 09/618,685, filed on Jul. 18, 2000, now abandoned, which is a continuation-in-part of application No. 09/159,467, filed on Sep. 23, 1998, now Pat. No. 6,261,241, and a continuation-in-part of application No. 09/196,125, filed on Nov. 20, 1998, now Pat. No. 6,454,727, and a continuation-in-part of application No. 09/057,303, filed on Apr. 8, 1998, now Pat. No. 6,331,166, and a continuation-in-part of application No. 09/717,176, filed on Nov. 16, 2000, now Pat. No. 6,497,706, which is a continuation-in-part of application No. 09/477,255, filed on Jan. 4, 2000, now Pat. No. 6,471,700.

(51) Int. Cl.[7] .............................................. A61B 10/00
(52) U.S. Cl. ........................ 600/564; 600/567; 606/167
(58) Field of Search ........................ 600/562, 564–567; 606/41, 45–50, 167, 170

(56) References Cited

U.S. PATENT DOCUMENTS

| | | |
|---|---|---|
| 2,032,860 A | 3/1936 | Wappler et al. |
| 2,192,270 A | 3/1940 | McGowan |
| 3,341,417 A | 9/1967 | Sinaiko |
| 3,805,791 A | 4/1974 | Seuberth et al. |
| 3,818,894 A | 6/1974 | Wichterle et al. |
| 3,823,212 A | 7/1974 | Chvapil |
| 3,847,153 A | 11/1974 | Weissman |
| 3,910,279 A | 10/1975 | Okada et al. |
| 3,955,578 A | 5/1976 | Chamness et al. |
| 4,007,732 A | 2/1977 | Kvavle et al. |
| 4,172,449 A | 10/1979 | LeRoy et al. |
| 4,197,846 A | 4/1980 | Bucalo |

(Continued)

FOREIGN PATENT DOCUMENTS

| | | |
|---|---|---|
| DE | 19528440 A1 | 8/1995 |
| DE | 192528440 A1 | 8/1995 |
| EP | 146699 | 9/1984 |

(Continued)

OTHER PUBLICATIONS

V. Fucci et al., "Large Bowel Transit Times Using Radiopaque Markers in Normal Cats", *J. Of Am. Animal Hospital Assn.*, Nov.–DEc. 1995 31 (6) 473–7.

(Continued)

*Primary Examiner*—Charles Marmor
(74) *Attorney, Agent, or Firm*—Edward J. Lynch; Duane Morris LLP

(57) ABSTRACT

Devices, methods and systems for obtaining biopsy tissue samples are provided. Flexible hollow tubes with a rail and a tip cutting element advance within a shaft with an aperture and a bore having a ramp, so that the cutting element emerges from the aperture and cuts tissue as it moves over the ramp. Either or both shaft and bore may have guides, which may engage each other to guide the tube along a tissue cutting pathway. A tube may have a rail and the bore a channel which engages the rail and guides the tube. Cut tissue may be acquired and transported proximally within the tube by suction to a tissue collection chamber. Multiple tissue samples may be obtained from a single insertion point by rotation and/or translation of the shaft between biopsies.

37 Claims, 9 Drawing Sheets

U.S. PATENT DOCUMENTS

| | | |
|---|---|---|
| 4,202,338 A | 5/1980 | Bitrof |
| 4,243,048 A | 1/1981 | Griffin |
| 4,276,885 A | 7/1981 | Tickner et al. |
| 4,294,241 A | 10/1981 | Miyata |
| 4,294,254 A | 10/1981 | Chamness |
| 4,311,143 A | 1/1982 | Komiya |
| 4,331,654 A | 5/1982 | Morris |
| 4,362,160 A | 12/1982 | Hiltebrandt |
| 4,418,692 A | 12/1983 | Guay |
| 4,503,855 A | 3/1985 | Maslanka |
| 4,545,367 A | 10/1985 | Tucci |
| 4,565,200 A | 1/1986 | Cosman |
| 4,576,162 A | 3/1986 | McCorkle |
| 4,638,802 A | 1/1987 | Okada |
| 4,647,480 A | 3/1987 | Ahmed |
| 4,693,237 A | 9/1987 | Hoffman et al. |
| 4,718,419 A | 1/1988 | Okada |
| 4,724,836 A | 2/1988 | Okada |
| 4,813,062 A | 3/1989 | Gilpatrick |
| 4,847,049 A | 7/1989 | Yamamoto |
| 4,863,470 A | 9/1989 | Carter |
| 4,909,250 A | 3/1990 | Smith |
| 4,926,858 A | 5/1990 | Gifford, III et al. |
| 5,007,908 A | 4/1991 | Rydell |
| 5,024,617 A | 6/1991 | Karpiel |
| 5,035,696 A | 7/1991 | Rydell |
| 5,047,027 A | 9/1991 | Rydell |
| 5,064,424 A | 11/1991 | Bitrolf |
| 5,066,295 A | 11/1991 | Kozak et al. |
| 5,078,716 A | 1/1992 | Doll |
| 5,080,660 A | 1/1992 | Buelna |
| RE33,925 E | 5/1992 | Bales et al. |
| 5,111,828 A | 5/1992 | Kornberg et al. |
| 5,133,359 A | 7/1992 | Kedem |
| 5,133,360 A | 7/1992 | Spears |
| RE34,056 E | 9/1992 | Lindgren et al. |
| 5,147,307 A | 9/1992 | Gluck |
| 5,158,561 A | 10/1992 | Rydell et al. |
| 5,163,938 A | 11/1992 | Kambara et al. |
| 5,196,007 A | 3/1993 | Ellman et al. |
| 5,197,846 A | 3/1993 | Uno et al. |
| 5,201,732 A | 4/1993 | Parins et al. |
| 5,201,741 A | 4/1993 | Dulebohn |
| 5,207,686 A | 5/1993 | Dolgin |
| 5,224,488 A | 7/1993 | Neuffer |
| 5,236,410 A | 8/1993 | Granov et al. |
| 5,258,006 A | 11/1993 | Rydell et al. |
| 5,281,218 A | 1/1994 | Imran |
| 5,281,408 A | 1/1994 | Unger |
| 5,282,781 A | 2/1994 | Liprie |
| 5,312,400 A | 5/1994 | Bales et al. |
| 5,318,564 A | 6/1994 | Eggers |
| 5,323,768 A | 6/1994 | Saito et al. |
| 5,324,288 A | 6/1994 | Billings et al. |
| 5,330,471 A | 7/1994 | Eggers |
| 5,334,381 A | 8/1994 | Unger |
| 5,335,671 A | 8/1994 | Clement |
| 5,344,420 A | 9/1994 | Hilal et al. |
| 5,368,030 A | 11/1994 | Zinreich et al. |
| 5,376,094 A | 12/1994 | Kline |
| 5,380,321 A | 1/1995 | Yoon |
| 5,395,312 A | 3/1995 | Desai |
| 5,395,319 A | 3/1995 | Hirsch et al. |
| 5,401,272 A | 3/1995 | Perkins |
| 5,415,656 A | 5/1995 | Tihon et al. |
| 5,417,687 A | 5/1995 | Nardella et al. |
| 5,417,697 A | 5/1995 | Wilk et al. |
| 5,422,730 A | 6/1995 | Barlow et al. |
| 5,423,814 A | 6/1995 | Zhu et al. |
| 5,431,649 A | 7/1995 | Mulier et al. |
| 5,433,204 A | 7/1995 | Olson |
| 5,437,665 A | 8/1995 | Munro |
| 5,441,498 A | 8/1995 | Perkins |
| 5,441,503 A | 8/1995 | Considine et al. |
| 5,462,553 A | 10/1995 | Dolgin |
| 5,470,308 A | 11/1995 | Edwards et al. |
| 5,477,862 A | 12/1995 | Haaga |
| 5,484,436 A | 1/1996 | Eggers et al. |
| 5,487,385 A | 1/1996 | Avitall |
| 5,494,030 A | 2/1996 | Swartz et al. |
| 5,501,654 A | 3/1996 | Failla et al. |
| 5,526,822 A | 6/1996 | Burbank et al. |
| 5,527,331 A | 6/1996 | Kresch et al. |
| 5,536,267 A | 7/1996 | Edwards et al. |
| 5,542,948 A | 8/1996 | Weavers et al. |
| 5,549,560 A | 8/1996 | Van de Wijdeven |
| 5,607,389 A | 3/1997 | Edwards et al. |
| 5,611,803 A | 3/1997 | Heaven et al. |
| 5,636,255 A | 6/1997 | Ellis |
| 5,643,246 A | 7/1997 | Leeb et al. |
| 5,643,282 A | 7/1997 | Kieturakis |
| 5,646,146 A | 7/1997 | Faarup et al. |
| 5,649,547 A | 7/1997 | Ritchart et al. |
| 5,665,085 A | 9/1997 | Nardella |
| 5,672,174 A | 9/1997 | Gough et al. |
| 5,674,184 A | 10/1997 | Hassler, Jr. |
| 5,676,925 A | 10/1997 | Klaveness et al. |
| 5,687,739 A | 11/1997 | McPherson et al. |
| 5,688,490 A | 11/1997 | Tournier et al. |
| 5,715,825 A | 2/1998 | Crowley |
| 5,720,763 A | 2/1998 | Tovey |
| 5,741,225 A | 4/1998 | Lax et al. |
| 5,766,169 A | 6/1998 | Fritzsch et al. |
| 5,769,086 A | 6/1998 | Ritchart et al. |
| 5,772,660 A | 6/1998 | Young et al. |
| 5,775,333 A | 7/1998 | Burbank et al. |
| 5,782,764 A | 7/1998 | Werne |
| 5,782,775 A | 7/1998 | Milliman et al. |
| 5,782,827 A | 7/1998 | Gough et al. |
| 5,794,626 A | 8/1998 | Kieturakis |
| 5,797,907 A | 8/1998 | Clement |
| 5,800,378 A | 9/1998 | Edwards et al. |
| 5,810,806 A | 9/1998 | Ritchart et al. |
| 5,853,366 A | 12/1998 | Dowlatshahi |
| 5,876,340 A | 3/1999 | Tu et al. |
| 5,882,316 A | 3/1999 | Chu et al. |
| 5,902,272 A | 5/1999 | Eggers et al. |
| 5,913,857 A | 6/1999 | Ritchart et al. |
| 5,925,044 A | 7/1999 | Hofmann et al. |
| 5,928,164 A | 7/1999 | Burbank et al. |
| 5,938,587 A | 8/1999 | Taylor et al. |
| 5,941,893 A * | 8/1999 | Saadat .................. 606/180 |
| 5,947,964 A | 9/1999 | Eggers et al. |
| 5,964,716 A | 10/1999 | Gregoire et al. |
| 5,972,002 A | 10/1999 | Bark et al. |
| 5,984,919 A | 11/1999 | Hilal et al. |
| 6,004,269 A | 12/1999 | Crowley et al. |
| 6,036,681 A | 3/2000 | Hooven |
| 6,050,992 A | 4/2000 | Nichols |
| 6,056,700 A | 5/2000 | Burney et al. |
| 6,059,782 A | 5/2000 | Novak et al. |
| 6,063,082 A | 5/2000 | DeVore et al. |
| 6,071,280 A | 6/2000 | Edwards et al. |
| 6,120,462 A | 9/2000 | Hibner et al. |
| 6,161,034 A | 12/2000 | Burbank et al. |
| 6,203,524 B1 * | 3/2001 | Burney et al. ............ 604/93.01 |
| 6,234,177 B1 | 5/2001 | Barsch |
| 6,254,601 B1 * | 7/2001 | Burbank et al. .............. 606/45 |
| 6,277,083 B1 | 8/2001 | Eggers et al. |
| 2001/0001811 A1 | 5/2001 | Burney et al. |
| 2002/0016555 A1 | 2/2002 | Ritchart et al. |

FOREIGN PATENT DOCUMENTS

| | | |
|---|---|---|
| EP | 0255123 | 2/1988 |
| EP | 0292936 | 11/1988 |
| EP | 0472368 A2 | 8/1991 |
| EP | 0481685 A1 | 10/1991 |
| EP | 0509670 A2 | 10/1992 |
| EP | 0667126 A1 | 8/1995 |
| EP | 0667126 | 8/1995 |
| EP | 0 919 190 A | 6/1999 |
| GB | 2311468 A | 2/1997 |
| WO | 93/14712 | 5/1993 |
| WO | 9313718 | 7/1993 |
| WO | 95/02370 | 7/1994 |
| WO | 95/02371 | 7/1994 |
| WO | 95/02370 | 1/1995 |
| WO | 95/02371 | 1/1995 |
| WO | 96/08208 A1 | 3/1996 |
| WO | 98/06346 | 2/1998 |
| WO | 98/08441 | 3/1998 |
| WO | 98/43531 | 10/1998 |
| WO | 99/30764 | 6/1999 |
| WO | 98/44506 | 9/1999 |
| WO | WO 99/44506 | 9/1999 |
| WO | WO 00/16697 | 3/2000 |
| WO | 00/16697 | 3/2000 |
| WO | WO 00/30531 | 6/2000 |
| WO | WO 02/05717 | 1/2002 |

OTHER PUBLICATIONS

N. E. Schindlbeck et al., "Measurement of Colon Transit Time", *J. of Gastroenterology*, No. 28, pp. 399–404, 1990.

Whitman et al., "Coaxial Core Nedle Biopsy Under Mammographic Guidance: Ihdications and Applications", *AJR*: 171, Jul. 1998, pp. 67–70.

International Search Report PCT/US99/04471, mailed Jun. 14, 1999.

International Search Report PCT/US01/00543, mailed Jul. 19, 2001.

International Search Report for PCT/US03/13520, mailed Dec. 17, 2003.

Armstrong J.S. et al., "Differential marking of excision planes in screened breast lesions by organically coloured gelantins [see comments].", *Journal of Clinical Pathology*, (Jul. 1990), 43(7) 604–7, XP000971447 abstract; tables 1 and 2.

F. Burbank, M.D., Stereotactic Breast Biopsy: Its History, Its Present, and Its Future, *The American Surgeon*, Feb. 1996, vol. 62, pp. 128–150.

The Loop Electrode: a New Device For US–guided Interstitial Tissue Ablation Using Radio frequency Electrosurgery—An Animal Study, 1996 Blackwell Science Ltd. *Min Incas Ther & Allied Technol*, pp. 5.511–516.

Timothy J. Micklos, Percutaneous Biopsy Techniques, *Manual of Oncologic Therapeutics* (1989/1990) pp. 39–42.

Whitman et al., Coaxial Core Needle Biopsy Under Mammographic Guidance: Indications and Applications, AJR:171, Jul. 1998, pp. 67–70.

English translation of German Application DE 195 28 440 A1, published Aug. 2, 1995.

International Search Report for PCT, US 99/21416 mailed May 19, 2000.

Written Opinion mailed Jul. 18, 2000, PCT Rule 66, for International Application PCT/US/9921416.

International Search Report for PCT, US 01/22894 mailed Nov. 21, 2001.

\* cited by examiner

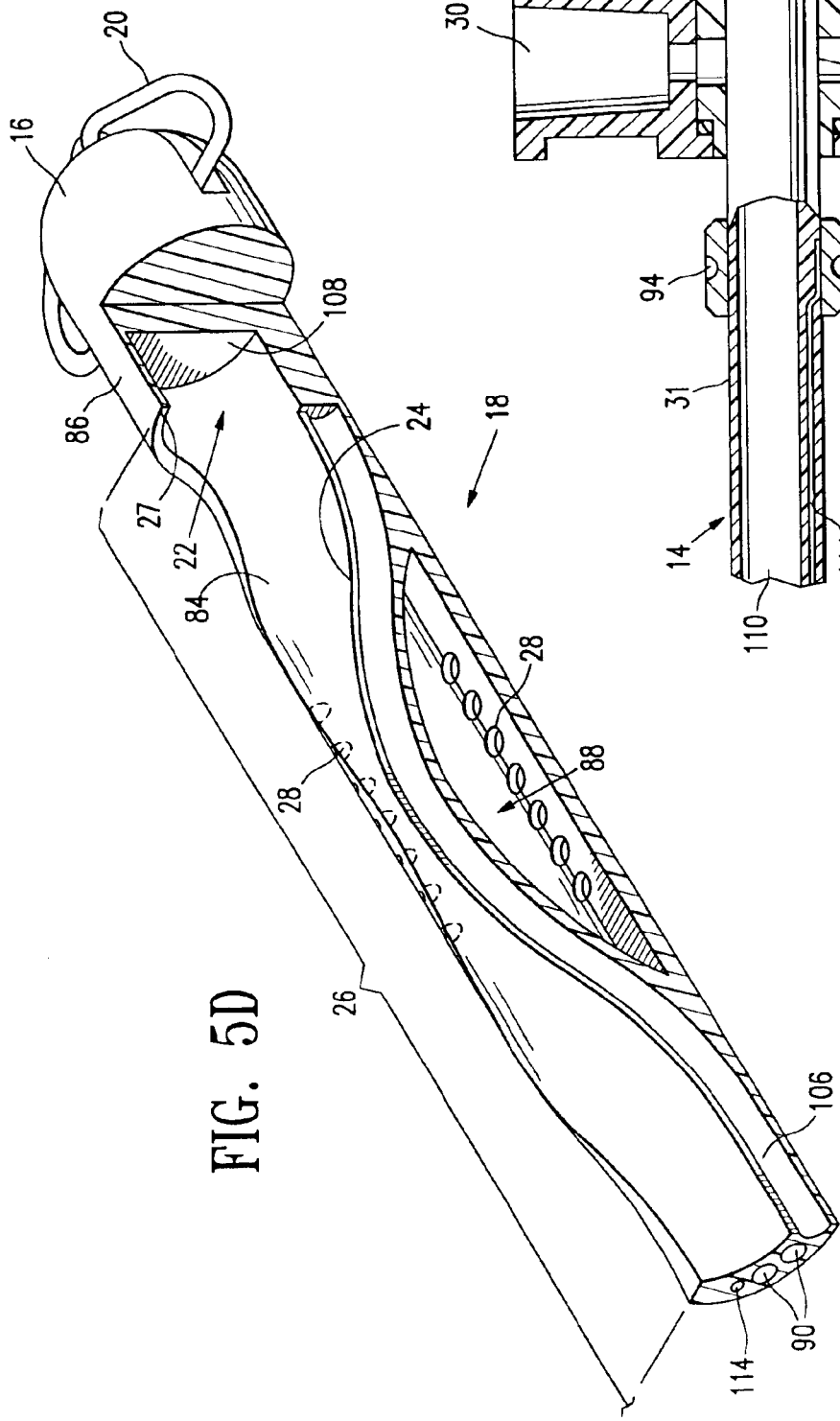

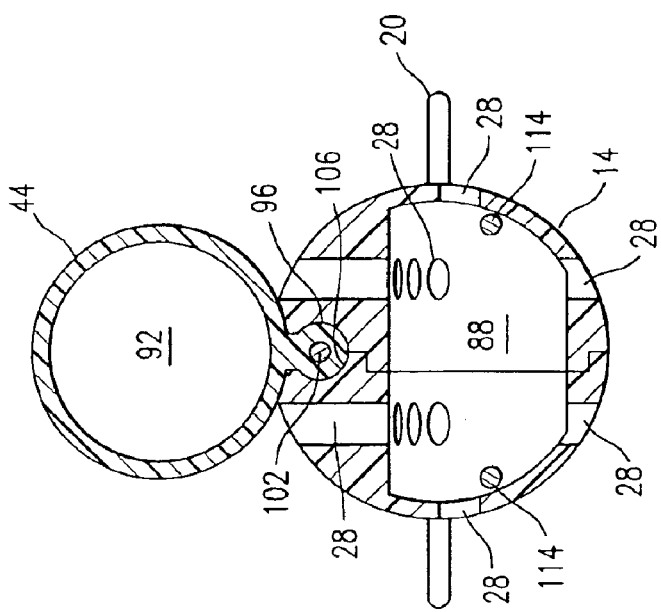
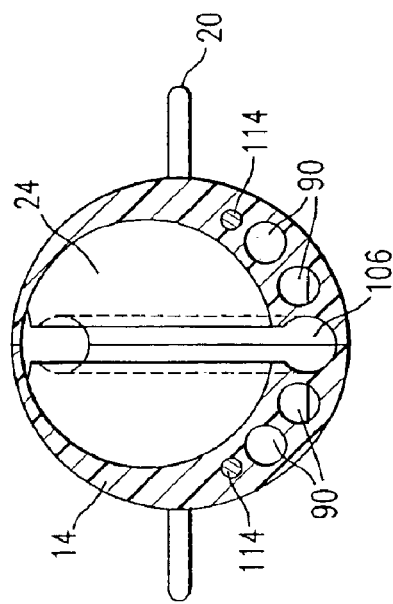
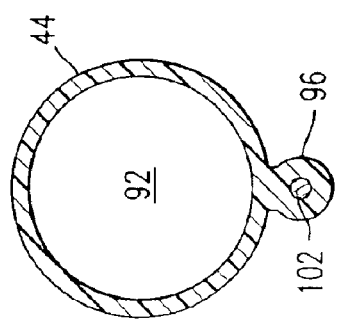
FIG. 6C
FIG. 6B
FIG. 6A

ELECTROSURGICAL SPECIMEN-COLLECTION SYSTEM

This application is a continuation-in-part of application Ser. No. 09/619,867, filed Jul. 20, 2000, now U.S. Pat. No. 6,517,498, which is a continuation of application Ser. No. 09/618,685, filed Jul. 18, 2000, now abandoned, which is a continuation-in-part of application Ser. No. 09/159,467, filed Sep. 23, 1998, now U.S. Pat. No. 6,261,241, application Ser. No. 09/196,125, filed Nov. 20, 1998, now U.S. Pat. No. 6,454,727, and application Ser. No. 09/057,303, filed Apr. 8, 1998, now U.S. Pat. No. 6,331,166, which claims benefit of provisional application Ser. No. 60/076,973, filed Mar. 3, 1998; and a continuation-in-part of application Ser. No. 09/717,176, filed Nov. 16, 2000, now U.S. Pat. No. 6,497,706, which is a continuation-in-part of application Ser. No. 09/477,255, filed Jan. 4, 2000, now U.S. Pat. No. 6,471,700, which are all hereby incorporated herein by reference in their entireties, and from all of which priority is hereby claimed under 35 U.S.C. §119(e) and §120.

FIELD OF THE INVENTION

This invention relates generally to the field of acquisition of tissue from a patient, as occurs in a biopsy procedure, in particular to the cutting and removal of tissue from the biopsy site.

BACKGROUND OF THE INVENTION

In diagnosing and treating certain medical conditions, it is often desirable to perform a biopsy, in which a specimen or sample of tissue is removed for pathological examination, tests and analysis. Typically, it is desired that biopsy material be taken from locations having characteristics indicating the presence of disease. For example, breast biopsies may be taken where a suspicious lump or swelling is noticed in a breast. As is known, obtaining a tissue sample by biopsy and the subsequent examination are typically employed in the diagnosis of cancers and other malignant tumors, or to confirm that a suspected lesion or tumor is not malignant. The information obtained from these diagnostic tests and/or examinations is frequently used to devise a plan for an appropriate surgical procedure or other course of treatment. Examination of tissue samples taken by biopsy is of particular significance in the diagnosis and treatment of breast cancer.

Thus, there is need in the art for devices and methods for collecting specimens from a biopsy site.

SUMMARY OF THE INVENTION

The present invention is directed to collecting tissue samples from a biopsy site within a patient. A biopsy device having features of the invention has an elongated shaft with an inner bore and an aperture, and an elongated cutting member with a flexible distal portion and a tissue cutting member on the distal end. The elongated cutting member is at least in part movably disposed within the bore of the elongated shaft. The elongated cutting member is preferably open-ended, and preferably has a guide configured to direct movement of the flexible distal end. The shaft may be inserted into a patient's body for removal of tissue, such as a biopsy sample. Distal movement of the elongated cutting member within the bore of the shaft allows the flexible distal end to emerge from the shaft aperture to cut surrounding tissue. Tissue samples may be transported proximally by suction within a hollow elongated cutting member for collection.

An embodiment of a biopsy device having features of the invention has an elongated shaft with an inner bore, a first guide extending along a distal shaft section which defines at least in part a tissue cutting pathway, and an elongated cutting member which is at least in part movably disposed within the bore of the elongated shaft. The elongated cutting member has a proximal section, a flexible distal section with an distal end and a tissue cutting member on the distal end. The elongated cutting member is preferably open-ended, with a second guide configured to engage the first guide on a distal section of the elongated shaft. The first and second guides cooperate to facilitate the movement of the elongated cutting member along the tissue cutting pathway.

In general, devices embodying features of the invention include an elongated shaft with an inner bore, and an elongated cutting member configured to move within the bore. The elongated cutting member is preferably a hollow tube, termed a tissue extraction tube, with a flexible distal portion, a distal opening, and a cutter disposed around the opening. The cutter may be on the rim of the opening, or may be spaced distally from it; preferably, the cutter is spaced away from the rim of the opening. The shaft may be relatively stiff in comparison to the elongated cutting member, and preferably has a cutting element on its distal tip to facilitate accessing the tissue site. A shaft cutting element may be a sharpened tip, a cutter configured to puncture or cut tissue, a radiofrequency (RF) cutter, or other cutting element. The shaft cutting element is preferably spaced a distance away from the distal tip of the shaft.

The shaft has a first guide, oriented in a substantially longitudinal direction, that is preferably disposed within the bore of the shaft. The elongated cutting member is configured to engage with the first guide, preferably with a cooperating second guide disposed on the elongated cutting member to facilitate following the tissue cutting pathway defined by the first guide. One of the guides may be, for example, a channel or slot, and the other guide may be, for example, a rail or a series of pins configured to slide within the channel or slot. The guides ensure that the motion of the elongated cutting member follows the desired tissue cutting pathway.

The shaft also has an aperture in a portion of the distal side wall connecting the shaft bore with a region outside the shaft. Although an opening, the aperture is taken to define an imaginary surface that is the continuation of the shaft wall. In addition, in shafts embodying preferred features of the invention, the shaft internal bore includes a ramp on an inner surface disposed substantially opposite the aperture. In preferred embodiments, as viewed from a proximal-to-distal perspective, the ramp rises within the bore from the inner surface towards an imaginary center-line within the shaft, and, in particularly preferred embodiments, past the center-line towards the open aperture, and then descends back to the level of the inner wall surface of the bore. Preferably, a first guide, such as a channel, is disposed along at least a portion of the ramp.

Elongated cutting members embodying features of the invention, such as tissue extraction tubes, are preferably configured to slide longitudinally within the bore of a shaft. In the following discussion, the elongated cutting member will be exemplified by a tissue extraction tube, although it will be understood that any elongated cutting member may be suitable. A second guide, such as a rail, is attached to at least a distal portion of the tube, and may extend along most or all of the length of the tube. In preferred embodiments, where the bore includes a ramp with a channel, and the tube has an attached rail engaged with the channel, longitudinal motion of a tissue extraction tube is guided by and follows the path defined by the channel. The flexibility of a tissue extraction tube embodying features of the invention allows it to substantially conform to the topography of the ramp. As such a tube moves distally within a bore having a ramp disposed opposite an aperture, the distal end of the tube rises, causing at least its distal tip to emerge from the shaft aperture under the guidance of the rail engaged with the channel. Further distal movement brings the distal end of the tube back down within the shaft again. In preferred embodiments, such distal movement places the distal tip of the hollow tube against the inner wall of the shaft distal tip within a structure termed a "cutting bowl."

Vacuum may be applied to a proximal portion of the tissue extraction tube to aspirate tissue specimens through the inner lumen of the tube. Systems include a carrier for mounting the shaft and for connecting the shaft and tube to a vacuum source and optionally to a radiofrequency power source.

Methods for removing a tissue specimen from within a patient's body include placing the shaft adjacent a tissue mass of interest located within a patient's body, advancing the tissue extraction tube, and cutting a tissue sample. In preferred methods, a RF cutter is activated and tissue is cut with a RF cutter. As described above, distal advancement of the tissue extraction tube moves the tube distal end and the loop cutter out of, and then back into, the shaft aperture. As the hollow tube passes through tissue, the cutter on the distal tip of the hollow tube cuts a path through the tissue, and severs the separated tissue from the tissue bed in the cutting bowl as it re-enters the shaft bore at the distal end of the ramp. Vacuum may be used to attract and hold tissue against the shaft and tube. Vacuum from the same or from a separate source may be applied to the proximal part of the hollow tube to transport the severed tissue specimen proximally to a tissue collection chamber. Tissue collection methods also include collection of multiple samples. Multiple samples may be taken at multiple locations distally or proximally along an axis, and may be taken at multiple radial locations around an axis. For example, the shaft and tube may be partially rotated about the longitudinal axis of the device by turning a thumbwheel to sever and collect a plurality of specimens about the longitudinal axis of the device. The amount of rotation may be an arbitrary amount and may be a preset amount. A preset amount of rotation about a longitudinal axis of a device may be, for example, designated by detents.

The need for separate collection and vacuum tubes is eliminated in the present invention since a tissue sample is vacuumed into a collection tube as soon as it is cut by a cutter at the opening of the tube. By cutting and collecting samples with a single flexible tube that emerges from an aperture in the wall of a shaft, biopsy samples may be collected with only a single small incision, thus minimizing trauma to the patient and eliminating the need for a separate vacuum or sample acquisition tube. Rotation of the shaft allows biopsy collection from diverse radial locations, thus maximizing the sample collection volume while maintaining the minimal level of patient trauma. Radiofrequency cutters such as a radiofrequency cutting loop on the distal end of the hollow tube allow the ready acquisition of tissue with little resistance from or deformation of the tissue during sample acquisition, insuring that the samples are actually taken from the expected locations.

These and other advantages will be further described in the following detailed description of embodiments of the invention. In the foregoing discussion, the primary biopsy site described is generally the human breast, although the invention may be used for collecting biopsy specimens from other parts of the human body and other mammalian body as well.

BRIEF DESCRIPTION OF THE DRAWINGS

FIG. 5D is a perspective, cross-sectional view of half of the distal tip of a tissue extraction tube embodying features of the invention.

FIG. 5E is a side, cross-sectional view of the proximal tip of an elongated shaft embodying features of the invention showing a vacuum connection and vacuum port and a radiofrequency electrode connection.

FIG. 6A is a transverse cross-sectional view of a tissue extraction tube with an attached rail embodying features of the invention taken along line 6A—6A of FIG. 4.

FIG. 6B is a transverse cross-sectional view of a shaft embodying features of the invention taken along line 6B—6B of FIG. 4 of the invention, showing vacuum ports, an internal bore and a channel running along the ramp seen distally of the section.

FIG. 6C is a transverse cross-sectional view of a shaft and a flexible tube taken along line 6C—6C of FIG. 3A with the tube in position along a channel on a ramp within the shaft.

DETAILED DESCRIPTION OF THE PREFERRED EMBODIMENTS

Figure 1:
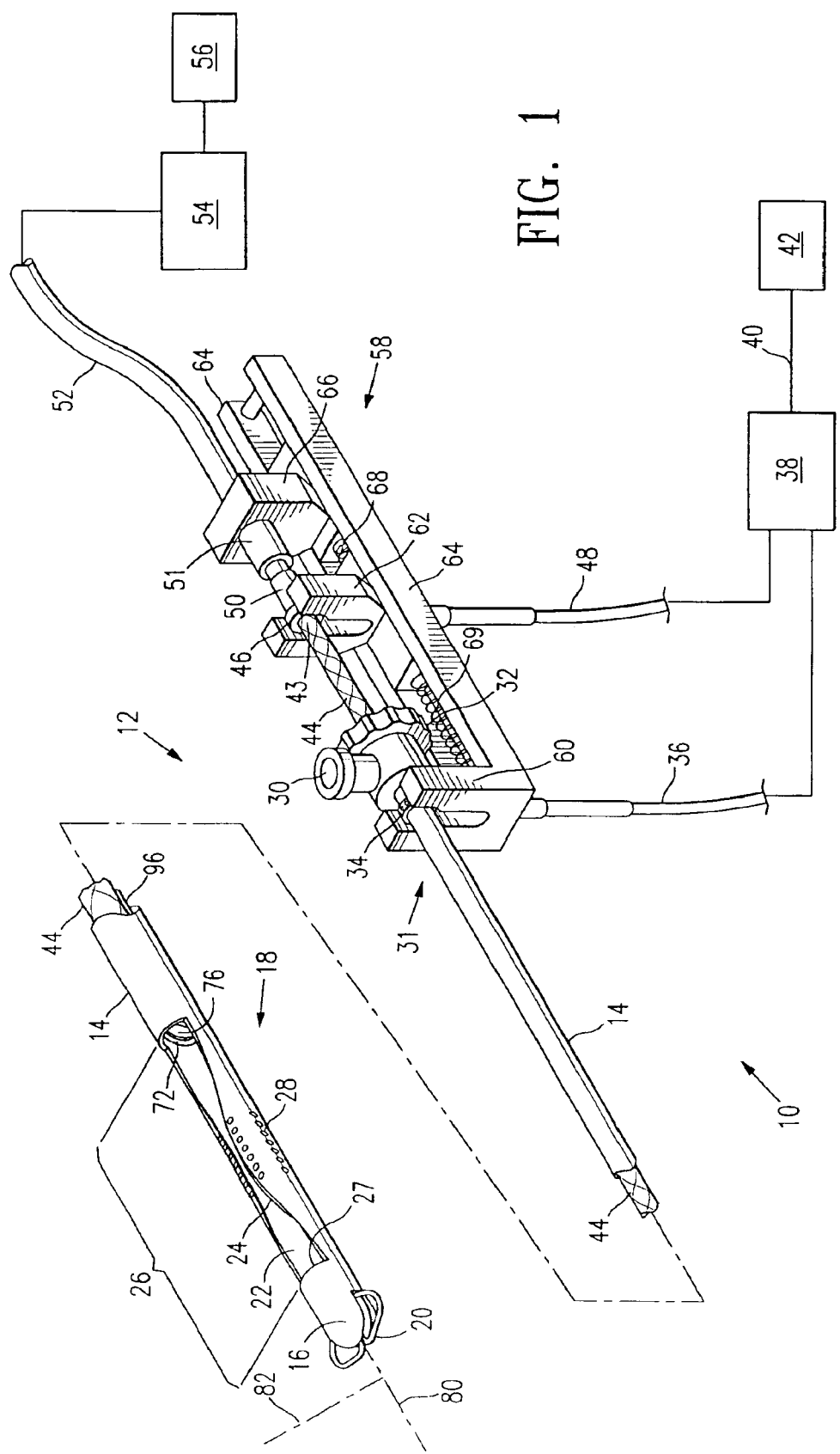
FIG. 1 is a perspective view of a system embodying features of the invention shown configured to begin taking a biopsy sample.

FIG. 1 is a perspective view of a system 10 embodying features of the invention, including a tissue acquisition assembly 12, a source of radiofrequency (RF) power 38 and a vacuum source 56. The tissue acquisition assembly 12 has a shaft 14 with a distal tip 16 at the end of distal portion 18. Shaft 14 preferably has a distal tip cutter 20 disposed on the distal tip 16. The shaft 14 is an elongated structure oriented along a longitudinal axis 80 that serves to define distal and proximal directions and a radial direction 82 perpendicular to axis 80. A center line within the shaft lies generally along axis 80.

Distal tip cutter 20 has a cutting surface effective to cut through tissue, opening up a path through which distal portion 18 of shaft 14 may be inserted, thus aiding in the placement of shaft 14 within a patient's body. A cutting surface may be any surface configured to cut tissue, e.g., by having a sharp edge, by having a thin cross-section, by being hard, by conducting radiofrequency energy, or by any combination of these or other properties. A cutter, or equivalently, a cutting element, may include supporting surfaces and structures in addition to cutting surfaces and structures. Distal tip cutter 20 is preferably spaced away from the shaft distal tip 16. Shaft 14 may have any cross-sectional shape, including round, square, hexagonal, or other shape. Where shaft 14 has circular cross-section, the width of shaft 14 is given by the radius of the circle. In further preferred embodiments, distal cutter 20 may extend radially to a distance greater than the width, or radius, of a shaft 14. Distal cutter 20 may also be made from multiple cutting elements; e.g., a distal cutter 20 embodying features of the invention may be made from a pair of wires configured to carry RF energy. For example, as shown in FIG. 1, and in greater detail in FIG. 2B, distal cutter 20 may include two curved wires configured to carry RF energy that are separated from, and extend distally from, shaft tip 16. Preferably, a pair of wires making up a distal cutter 20 are oriented substantially along a plane, most preferably a plane including a diameter of a shaft 14, so that the wires extend in directions separated by about 180°. Cutting elements, such as a wire or wires, making up a distal cutter 20 may be rigidly mounted to a distal tip 16, or may be flexibly mounted to a distal tip 16. For example, a flexibly mounted cutting element may spring back outwardly to a deployed configuration after having been inwardly compressed within a cannula.

The shaft distal portion 18 also includes a cutting bowl 22 and a ramp guide 24, visible through aperture 26, which provides access to them. A ramp guide 24 may be any structure within a shaft 14 having a surface with contours that include tangents not substantially parallel to a shaft longitudinal axis. Such a surface may be termed a non-axial surface. The inner radius of the shaft bore thus changes in a longitudinal direction along the length of a ramp disposed within the bore of the shaft. A ramp guide 24 may have a flat surface, having parallel tangent lines when tangents are taken at various positions along the ramp guide 24; such a flat ramp guide 24 may be termed a linear non-axial surface. Alternatively, a ramp guide 24 may have a curved surface, having tangent lines that are not parallel when tangents are taken at various positions along the ramp guide 24. A ramp guide 24 having such a curved surface may be termed a non-linear non-axial surface. In preferred embodiments, a ramp guide 24 includes non-linear non-axial surface portions. For example, the ramp guide 24 shown in FIGS. 2A and 2B has a non-linear non-axial surface.

The ramp guide 24 is shown rising from within the shaft to a level near that of the level of the aperture 26. The level of an aperture 26 is taken to be the level of the surrounding wall surface extended across the opening of the aperture 26. Where the surrounding wall is curved, the extension of the curved surface is also taken to have the same curvature. A ramp guide 24 may be entirely below the level of the aperture 26, or may rise to a level equal to, or greater than, the level of the aperture 26.

Cutting bowl 22 is bounded proximally by ramp guide 24 and is defined radially by shaft inner wall 84. Aperture 26 is an opening in the wall of shaft 14, shaft outer wall 86 extending from all directions to the aperture edge 27. Vacuum vents 28, shown here disposed on shaft distal portion 18 near aperture 26, are useful for pulling and holding tissue against shaft 14 and cutting bowl 22 when a shaft 14 is placed within a patient's body.

A vacuum inlet connector 30 is disposed on a proximal portion 31 of shaft 14 for connecting to a vacuum line connected to a source of vacuum for providing vacuum to vacuum vents 28. Thumbwheel 32, also disposed on shaft proximal portion 31, enables an operator to manually rotate shaft 14 around longitudinal axis 80 to orient aperture 26 so that it opens in a variety of radial directions 82 towards body tissue surrounding shaft 14. RF connector 34 provides RF energy to cutting element 20. RF connector 34 may be configured to provide RF power during rotation of the shaft, for example, where RF connector 34 is a conductive ring as shown in FIG. 1. RF cable 36 leads to RF power source 38. Radiofrequency cutters may be monopolar or bipolar; a monopolar cutting surface is connected to one conductor leading to a source of radiofrequency energy, and requires a separate ground or indifferent electrode to be placed in contact with a patient's body in order to cut a patient's body tissue. A bipolar radiofrequency cutting surface includes at least two conductors, each connected to different conductors connected to a radiofrequency energy source, so that the bipolar radiofrequency cutting surface does not require a separate ground or indifferent electrode in order to operate. Where distal cutter 20 is a monopolar RF cutter, RF power source 38 may be connected to conductor 40 and ground pad 42 which may be placed in electrical contact with a patient's body to provide a complete electrical circuit. Where distal cutter 20 is a bipolar RF cutter, conductor 40 and ground pad 42 are not necessary.

Tissue acquisition assembly 12 also includes a tissue extraction tube 44 configured to slide into shaft 14. An exposed proximal portion 43 of a tissue extraction tube 44 having features of the invention is shown in FIG. 1. RF connection 46, which carries RF energy obtained from an operable electrical connection to RF cable 48 leading to RF power source 38, provides RF energy to tissue extraction tube 44. Tube 44 has a vacuum connector 50 disposed on its proximal portion 43 that is configured to mate with a complementary vacuum connector 51 which provides an operable connection to vacuum line 52 connected to vacuum source 56. Vacuum line 52 is preferably a flexible vacuum hose. Vacuum applied to the tissue extraction tube 44 is effective to draw tissue towards the tube 44 and to transport severed tissue samples within the hollow tissue extraction tube 44 towards the vacuum source 56. A tissue collection chamber 54 may be placed in or near the vacuum line 52 or vacuum source 56 in order to retain tissue samples for analysis.

Thus, a tissue extraction tube 44 is preferably a hollow elongated tubular member with openings at both ends that is configured to sever a sample of tissue from within a body. A tissue extraction tube 44 may be used to acquire biopsy samples from a patient and may also be used to transport a tissue sample out of the body to, for example, a tissue collection chamber. A center line within a tube 44 lies generally along a local longitudinal axis. The center line of one portion of a straight tube is also a center line for other portions of that straight tube. A tissue extraction tube typically has a flexible portion and is capable of assuming a non-linear configuration during use (it may bend or curve), such that at least a portion of the tube wall may approach or cross a center line defined by another portion of the tube. The flexible part of a tissue extraction tube may be limited to only a portion, such as a distal portion; alternatively, a tissue extraction tube may be flexible along its entire length.

A shaft 14 and tissue extraction tube 44 embodying features of the invention may be mounted onto a support frame 58 effective to secure and guide them before, during, and after tissue sample collection. The support frame 58 illustrated in FIG. 1 includes a distal brace 60 configured to hold a shaft 14 while allowing its rotation and a proximal brace 62, configured to hold a tube 44. Braces 60 and 62 are configured to hold shaft 14 and tube 44 while allowing their rotation. Braces 60 and 62 may include snap connectors or other mechanisms configured to provide both mechanical support and electrical contact. Proximal brace 62 is configured to move longitudinally along support beams 64 while being substantially prevented from lateral (radial) movement. Similarly, vacuum support 66 is configured to move freely along support beams 64 in longitudinal directions but not in radial directions. It will be understood that, in embodiments of the invention, a single support beam 64, or a plurality of support beams 64 may be used to hold and guide either or both of a brace 62 and a support 66. In preferred embodiments, and as illustrated in FIG. 1, springs 68 (between proximal brace 62 and vacuum support 66) and 69 (between distal brace 60 and proximal brace 62) aid in proper positioning of components at rest and during use. Springs 68 and 69 are configured to apply forces so that when removal of forward pressure, the tissue extraction tube 44 and proximal brace 62 automatically retract. Spring 69 is preferably stronger than spring 68 in order to insure that the connection with vacuum source 56 is maintained while cutting. Spring 68 also cushions contact between proximal brace 62 and vacuum support 66. Vacuum line 52, being connected to vacuum support 66, is carried along by any longitudinal movement of vacuum support 66, maintaining its operable connection to vacuum source 56 and tissue collection chamber 54 even during movement of the tissue extraction tube 44.

As illustrated in FIG. 1, shaft 14 and tissue extraction tube 44 may be configured so that distal movement of the vacuum support 66 towards proximal brace 62 brings spring 68 into contact with proximal brace 62, urging proximal brace 62 distally towards distal brace 60, to compress spring 69 and to move tissue extraction tube 44 distally within shaft 14.

Figure 2A:
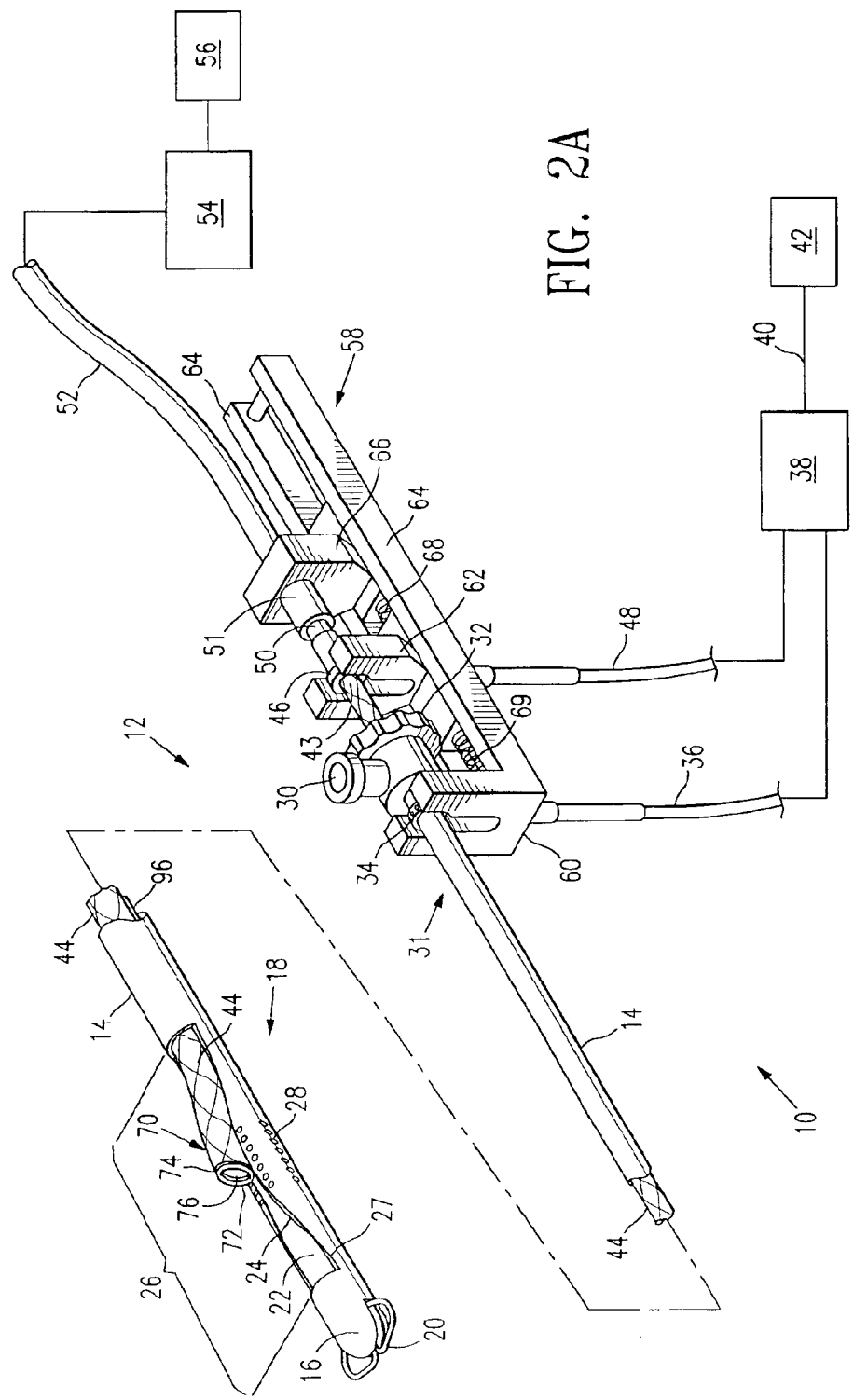
FIG. 2A is a perspective view of a system embodying features of the invention, showing the flexible distal portion of a tissue extraction tube emerging from the aperture.
Figure 2B:
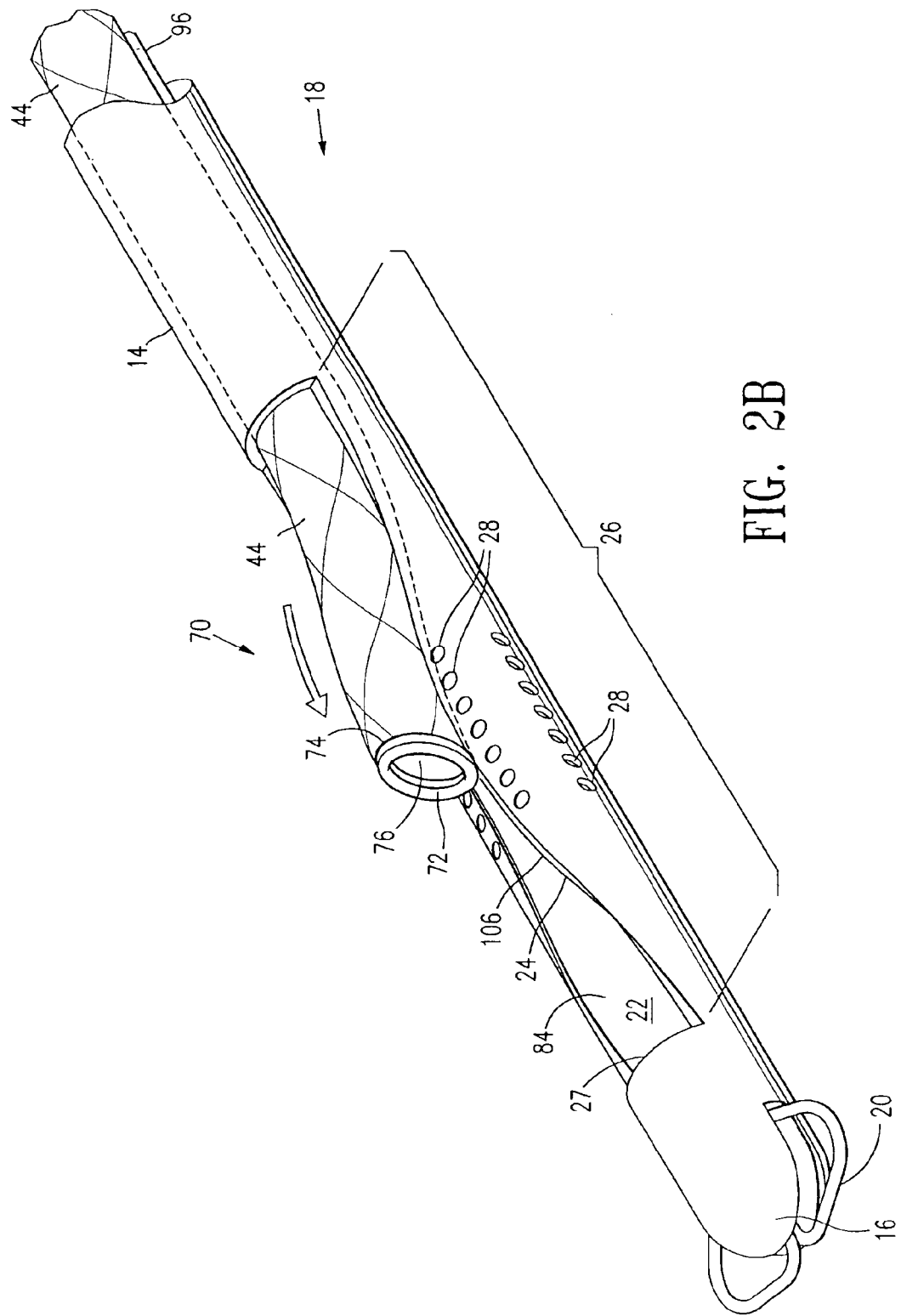
FIG. 2B is a detailed perspective view of the distal portion of the shaft and tube of the device shown in FIG. 2A showing the advancing distal end of the flexible tube in cutting position along the tissue cutting pathway defined in part by the ramp.

As illustrated in FIGS. 2A and 2B, longitudinal movement of a tissue extraction tube 44 within a shaft 14 causes the distal portion 70 of tube 44 to travel along ramp guide 24 and to emerge from aperture 26. Vacuum vents 28 are disposed along shaft outer wall 86 at locations near the aperture edge 27 adjacent aperture 26 and at locations somewhat removed from aperture 26. Vents 28 serve to attract and hold tissue near to the distal portion 18 of shaft 14 and to cutting bowl 22.

The distal portion of tube 44 includes a loop cutter 72 disposed on the rim 74 of the orifice 76 leading into the hollow interior 92 of tube 44. Loop cutter 72 may be any cutting element, such as a sharp blade; however, loop cutter 72 is preferably a RF cutter, such as a loop of conducting wire operably connected to a RF power source 38. A loop cutter may be formed from any loop-shaped cutting surface, such as a wire, band, ribbon or strip of material, shaped as a loop, whether circular, elliptical, polygonal, or irregular in cross-section. A loop cutter 72 may be a continuous loop in the shape of a closed loop, or may be discontinuous, in the shape of a partial loop such as a loop with ends that do not fully connect with one another, or be made up of more than one separate cutting elements arrayed about the rim 74 of an orifice 76 in a loop shape. In some embodiments, a loop cutter 72 may be spaced distally from the rim 74 of orifice 76. A cutter support 73 or plurality of cutter supports 73 may connect with a cutter 72 in order to support a cutter 72 at a position distal to the rim 74 of an orifice 76.

When supplied with RF power, or when it includes a sharp cutting edge, or other cutting element, loop cutter 72 is effective to cut body tissue with which it comes into contact. Insertion of a distal portion 18 of shaft 14 into a patient's body, and the application of suction through vacuum vents 28 and tube orifice 76, are each effective to bring tissue into contact with a cutting loop 72 disposed outside an aperture 26. Movement of loop cutter 72 through body tissue is effective to cut a portion of body tissue. The body tissue may be drawn into orifice 76 by action of the forward (distal) motion of tube 44 and by suction from vacuum source 56 applied by vacuum line 52 to vacuum inlet connector 50 and to the hollow interior 92 of tube 44. Thus, when a shaft 14 holding a tissue extraction tube 44 is disposed within a patient's body, forward motion of tube 44 along ramp guide 24 bringing cutting loop 72 into contact with body tissue adjacent shaft distal portion 18 is effective to cut a swath or strip of tissue from within a patient's body.

As shown in FIG. 2B, viewed from a proximal to distal direction, ramp guide 24 angles upward to a maximum and then descends again into cutting bowl 22 defined proximally by the ramp and radially by shaft inner wall 84. Tube 44 is shown angling upward with its distal tip 74 and orifice 76 positioned approximately mid-way along the ramp guide 24. This corresponds to a configuration where vacuum tube support 66 and proximal brace 62 are situated approximately mid-way along the extent of their effective longitudinal travel distance on support beams 64.

Cutting loop 72 moves through tissue adjacent aperture 26 as tissue extraction tube 44 moves in a distal direction along ramp guide 24. The path taken by cutting loop 72 is determined by the guides of the shaft 14 and of tube 44, such as channel 106 and rail 96, which constrain the motion of tube 44 and of cutting loop 72 along a tissue cutting pathway defined by channel 106, the shaft guide shown in FIG. 2B. The orientation of shaft 14 within a patient's body, including the radial orientation of aperture 26, thus determines the point of origin of the tissue samples removed from the patient.

FIG. 2B also shows guides rail 96 and channel 106, which are shown in greater detail in later figures. Rail 96 is attached to tube 44, and engages channel 106 so that movement of tube 44 is constrained in radial directions, but not longitudinal directions, by the tissue cutting pathway defined by channel 106. Thus, when engaged with a channel 106, a rail 96 follows the tissue cutting pathway defined by the channel 106. As shown in FIG. 2B, channel 106 lies along ramp guide 24 and along shaft inner wall 84 within shaft 14, and follows the contours of shaft inner wall 84 and ramp guide 24; in particular, in the region of ramp guide 24, channel 106 defines a non-linear non-axial pathway within shaft 14. The engagement between rail 96 and channel 106 is effective to guide tube 44 up the ascending portion of ramp guide 24 and down the descending portion of ramp guide 24 as tube 44 moves in a distal direction past the position shown in FIG.

2B. In general, a rail 96 may be any elongated element configured to engage a channel 106. A channel 106 is typically much longer than it is wide, its length defining a longitudinal direction and its width defining a radial direction. A rail 96 engaged with a channel 106 is able to move readily in a longitudinal direction, while its motion in a radial direction is constrained by the channel 106. These directions may be applicable to the entire channel 106, if the channel 106 is straight, or may be merely local directions, if the channel 106 is curved.

Figure 3A:
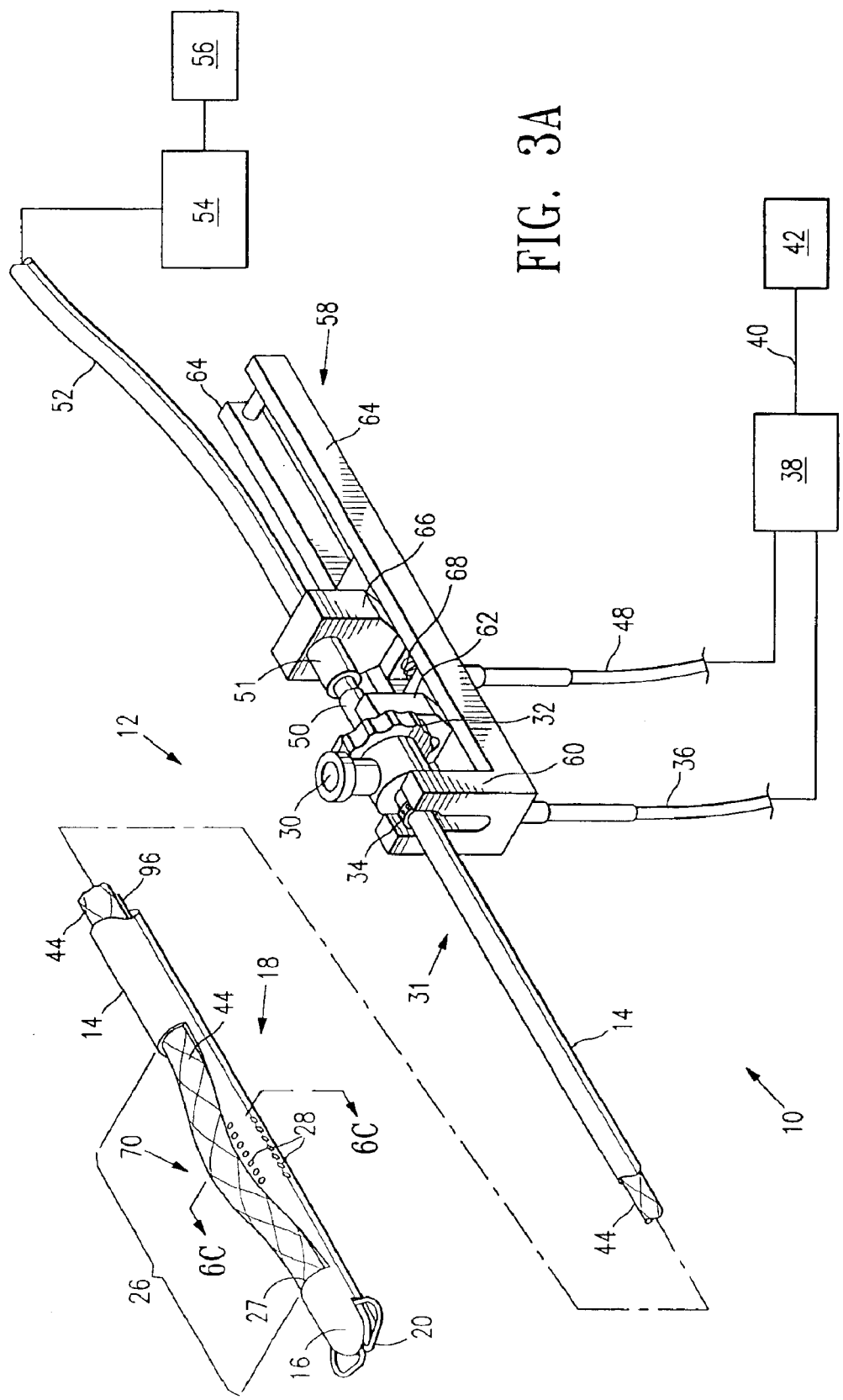
FIG. 3A is a perspective view of the device of FIGS. 1 and 2 configured with the tissue extraction tube fully advanced within the shaft, with the distal tip of the flexible tissue extraction tube fully extended past the aperture into the cutting bowl.
Figure 3B:
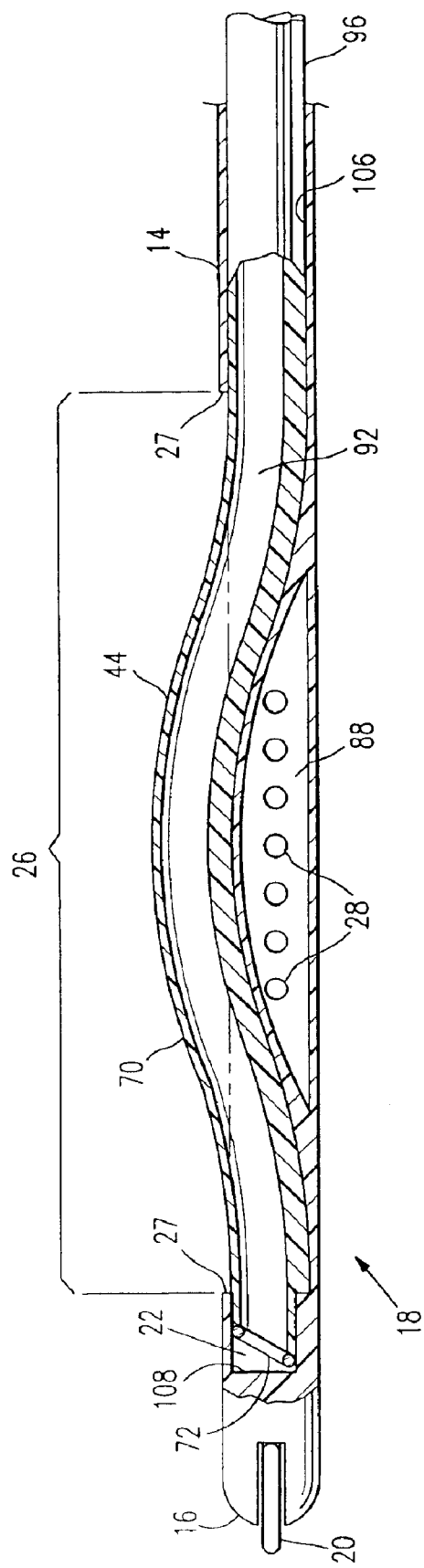
FIG. 3B is a longitudinal cross-sectional view of the distal portion of the shaft and tube of the device shown in FIG. 3A showing the distal end of the flexible tube fully extended along the tissue cutting pathway over the ramp with its distal tip within the cutting bowl at the distal end of the aperture, after it has cut a tissue specimen.

In FIGS. 3A and 3B, tube 44 is shown advanced to a maximal distal extent. Tube 44 follows an arc-like path as it climbs up and then down along the ramp guide 24. As shown in FIG. 3A, vacuum tube support 66 and proximal brace 62 have moved distally to the full extent of their effective longitudinal travel distance on support beam** 64, pushing tube 44 to its full travel within shaft 14, out of aperture 26, and placing at least part of tissue extraction tube distal portion 70 into cutting bowl 22. A ramp embodying features of the invention may have any contour effective to expose a cutting loop 72 to body tissue as a tube 44 moves longitudinally along a tissue cutting pathway lying on or along the ramp. A ramp guide 24 may ascend and descend with little or no transition portion between ascending and descending portions, or may alternatively include an extended level plateau portion between ascending and descending ramp portions. In such alternative configurations, a tube 44 assumes a configuration conforming to that ramp profile by angling upward, lying level over the plateau portion, and then angling downward into the cutting bowl 22 at its most distal extent.

As loop cutter 72 advances in a distal direction along ramp guide 24, cutting a swath of tissue from a tissue bed, a distal, connecting portion of the tissue swath remains attached to the body tissue mass. However, the loop cutter 72 descends into cutting bowl 22 as it advances along the distal, descending portion of ramp guide 24 near its maximal distal travel. As shown in FIG. 3B, within the cutting bowl 22, the loop cutter 72 is no longer in contact with the tissue bed adjacent the shaft distal portion 18. The descent of loop cutter 72 into cutting bowl 22, past aperture edge 27 severs the connecting portion of the tissue swath, freeing the swath of body tissue from the tissue bed and providing an isolated tissue sample. Vacuum within tube 44 draws the tissue sample proximally within the hollow interior 92 of tube 44 into vacuum line 52 and to tissue collection chamber 54.

Cutting loop 72 disposed on tube rim 74 is illustrated in cross-section within cutting bowl 22 in FIG. 3B. In that figure, tube 44 assumes an arc-like configuration along ramp 44, with a part of distal tube portion 70 within cutting bowl 22. That position may be achieved by distal movement of cutting loop 72 from a position where orifice 76 is outside aperture 26 to a position where orifice 76 passes aperture edge 27 to assume a position within cutting bowl 22 as shown in the figure. Distal movement of orifice 76 and cutting loop 72 past aperture edge 27 is effective to sever the strip of tissue connecting a tissue swath with the external tissue bed adjacent shaft distal portion 18. FIG. 3B also shows vacuum chamber 88 which supplies vacuum vents 28. The connection of vacuum chamber 88 to vacuum port 30, provided by vacuum ports 90, is illustrated in FIGS. 5D and 6B.

Figure 4:
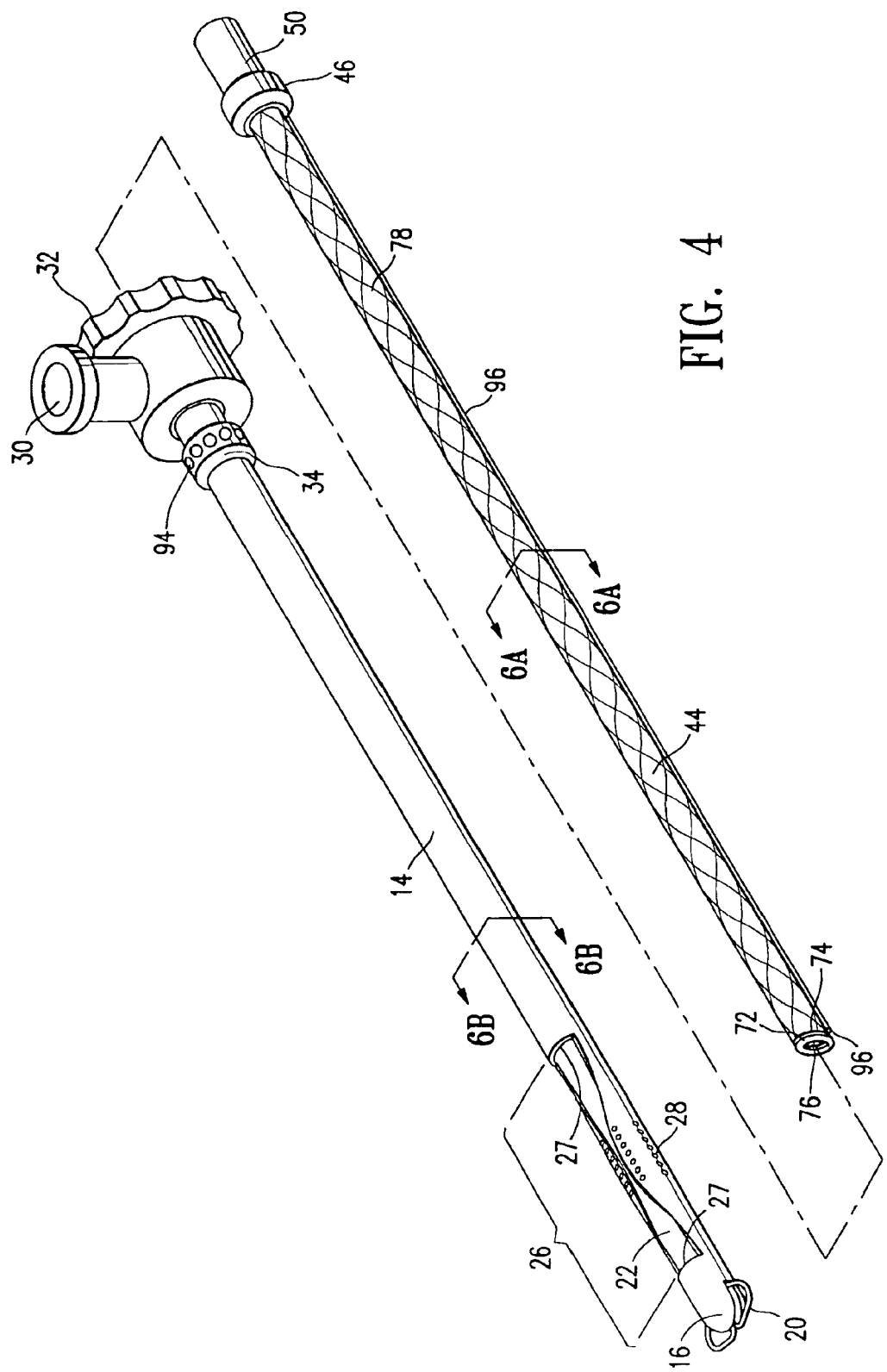
FIG. 4 is a perspective view of a shaft and of a flexible tissue extraction tube embodying features of the invention shown lying next to each other in positions corresponding to the relative positions taken by these elements when in place in the assembled device.

FIG. 4 shows shaft 14 and tissue extraction tube 44 disposed along side one another. Tissue extraction tube 44 is preferably somewhat longer than shaft 14, so that tube 44 may be inserted within shaft bore 110 with tube distal portion 70 fully extended into cutting bowl 22 and still allow proximal end 43 of tube 44, with its vacuum connection 50, to extend proximally beyond the vacuum connection 30 and thumbwheel 32 at shaft proximal portion 31. FIG. 4 also illustrates optional radial indents 94 on RF connector 34 which may be used to help to hold shaft 14 in a desired radial orientation after rotation of the shaft 14, as by turning thumbwheel 32. Pins, detents, or other devices may be used to engage indents 94 effective to secure the position of shaft 14.

FIG. 4 also shows rail 96 attached to tube 44. As illustrated in this figure, rail 96 extends along the length of tube 44; however, in other embodiments, a rail 96 may extend along only a distal portion of tube 44 and may be absent along a proximal portion 43 of a tissue extraction tube 44. A rail 96 is securely attached to tube 44, and in some embodiments of the invention may be an integral part of a tube 44. Control of the movement of a rail 96 is also effective to control the movement of a tube 44 to which is attached or of which it is a part. Thus, engagement of a rail 96 with a channel 106 is effective to guide the movement of a tube 44 along a ramp guide 24. For example, rail 96 is effective to guide tissue extraction tube 44 into the arc-shaped path lying over ramp guide 24 as illustrated in FIGS. 2A–2B and 3A–3B.

Figure 5A:
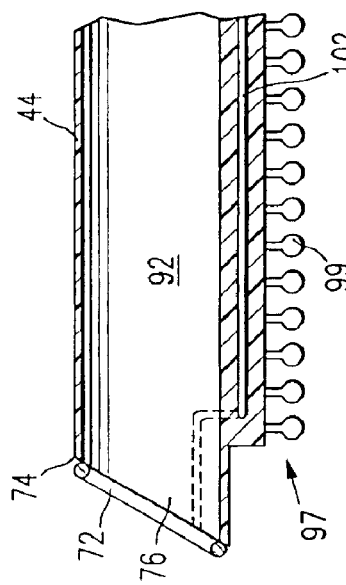
FIG. 5A is a side, cross-sectional elevation view of the distal tip and loop electrode of a tissue extraction tube embodying features of the invention.

A distal portion 70 of a tissue extraction tube 44 embodying features of the invention is shown in FIG. 5A. The orifice 76 of tube 44 leads in a proximal direction to tube bore 92; loop cutter 72 is disposed on rim 74 of tube 44 and about the orifice 76 in the embodiment shown in FIG. 5A. The loop diameter 98 of loop cutter 72 is preferably smaller than the inner diameter 100 of orifice 76, insuring that the dimensions of a tissue swath cut by loop cutter 72 are small enough to fit within tube bore 92. As illustrated in FIG. 5A, cutting loop 72 is connected to tube RF connection wire 102 which runs in a longitudinal direction along tube 44 within rail 96.

Figure 5B:
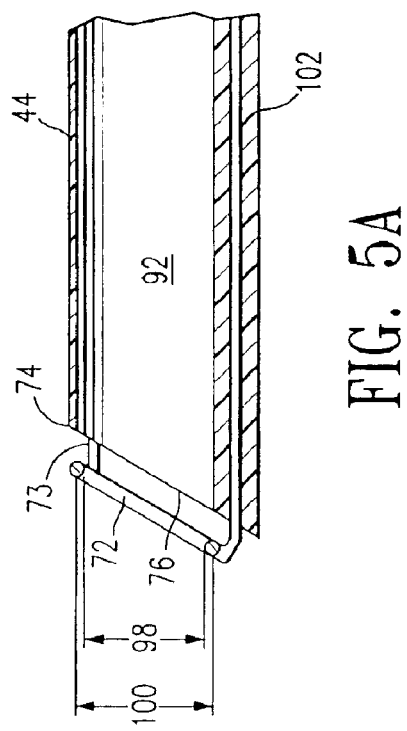
FIG. 5B is a side, cross-sectional elevation view of the distal tip and loop electrode of an alternative embodiment of a tissue extraction tube embodying features of the invention.

An alternative tube guide 97 is shown in FIG. 5B. A series of pins 97 having heads 99 are disposed in a linear arrangement along a surface of a tube 44. Pins 97 and heads 99 are configured to fit into and engage a shaft guide, such as a channel 106 as illustrate in other Figures, effective to guide movement of a tube 44 along a tissue cutting passage.

Figure 5C:
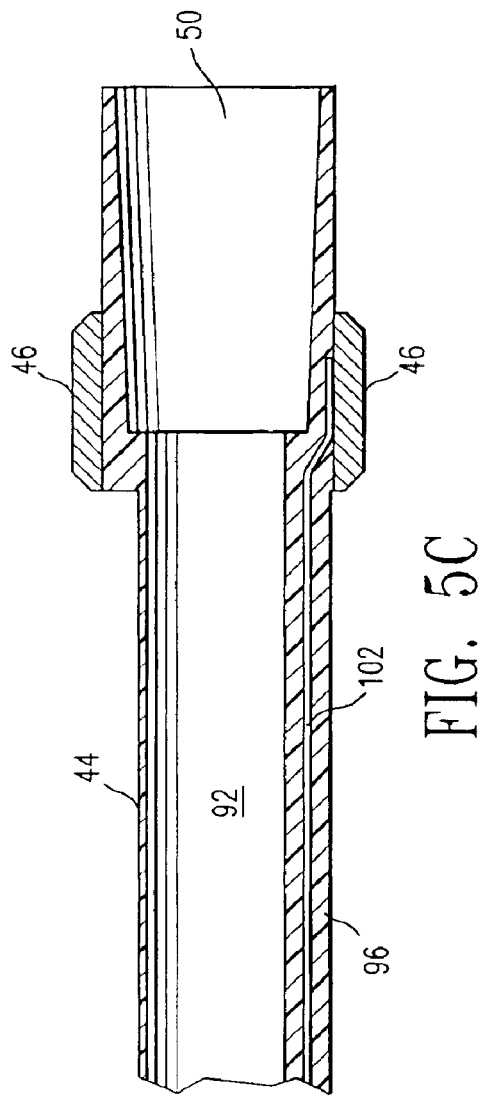
FIG. 5C is a side, cross-sectional elevation view of the proximal tip of a tissue extraction tube embodying features of the invention showing a luer lock vacuum connection and a conductor for connecting a radiofrequency electrode connection to a source of radiofrequency power.

A proximal portion 43 of a tissue extraction tube 44 embodying features of the invention is shown in FIG. 5C. In this embodiment, rail 96 (including RF connection wire 102) extends along the entire length of the tube 44. External RF connector 46, which includes a conductive ring around the diameter of tube 44, is operably connected to RF connection wire 102 as shown, allowing tube 44 to rotate while maintaining effective electrical contact with RF power source 38. FIG. 5C also illustrates a luer lock vacuum connection 50 configured to engage a vacuum connection 51 or vacuum line 52 leading to a vacuum source 56, effective to supply vacuum to tube bore 92.

As illustrated in FIG. 5D, a cutting bowl 22 within the shaft distal portion 18 has a distal inner wall 108 which serves to limit the distal movement of a tube 44 disposed within a bore 110 of a shaft 14 embodying features of the invention. Shaft inner wall 84 forms the remainder of the boundary defining cutting bowl 22, while shaft outer wall 86 extends up to aperture edge 27 to define the outer surface of shaft 14 and the outer perimeter of aperture 26. This figure also shows vacuum chamber 88 which provides vacuum to vacuum vents 28. Vacuum vents 28 aid in drawing tissue to shaft 14 so that a cutting loop 72 has sufficient nearby tissue from which to cut a tissue sample. Vacuum ports 90 within shaft 14 connect vacuum chamber 88 with vacuum source 56 via vacuum connections 50 and 51 and via vacuum line 52.

The proximal portion 31 of a shaft 14 embodying features of the invention is illustrated in FIG. 5E, showing RF connector 34 operably connected to shaft RF wire 114 to provide an electrical connection effective to supply RF power to distal cutter 20. As shown, vacuum connector 30 leads to vacuum port 90 so that vacuum provided through connector 30 has access to vacuum port 90 at all radial orientations of shaft 14. O-ring 112 provides a vacuum-tight seal allowing rotation of shaft 14 while maintaining an effective vacuum connection.

Transverse cross-sections of a tube 44 and shaft 14 embodying features of the invention are shown in FIGS. 6A–6C. FIG. 6A shows a transverse cross-section of a tube 44 taken along line 6A—6A of FIG. 4, and illustrates a suitable configuration for the attachment of a rail 96 with a tube 44. Tube electrode wire 102, which supplies cutting loop 72 with RF power, is insulated by the non-conductive material of rail 96 surrounding it, and also provides strength to rail 96. As shown in FIG. 6B, illustrating a transverse cross-section of a shaft 14 taken along line 6B—6B of FIG. 4, vacuum ports 90 and shaft electrode wires 114 (which provide RF power to distal cutter 20) may be disposed within the wall of shaft 14. Ramp guide 24 and channel 106 may also be seen in FIG. 6B, which is a view looking in the distal direction.

FIG. 6C is a transverse cross-sectional view, taken along line 6C—6C of FIG. 3A, of a shaft 14 and a tube 44 engaged together. The cross-section of FIG. 6C is taken at a position where the ramp guide 24 has risen to a level near to the level of aperture 26, exposing tube 44 to a maximal extent to the region outside the shaft 14. Thus, tissue extraction tube 44 is shown in cross-section in FIG. 6C at the point of its greatest excursion out of bore 110 outside aperture 26, at the peak of ramp guide 24. Such radial excursion of the tube 44 outside the aperture 26 is effective to allow loop cutter 72 to cut tissue from regions surrounding shaft 14. Rail 96 remains engaged with channel 106 during longitudinal movement of tube 44, and such engagement is effective to guide distal portions of tube 44 down a distal portion of ramp guide 24 into cutting bowl 22. FIG. 6C also shows the vacuum chamber 88 disposed below ramp guide 24 and channel 106. Shaft electrode wires 114 leading to distal cutter 20 are also shown, as are vacuum vents 28.

The invention provides assemblies, devices, and systems for obtaining tissue samples from within a patient's body. Assemblies 12 include shafts 14 and tissue extraction tubes 44 having features of the invention, with tubes 44 disposed at least in part within shafts 14 for example, as described above. Systems 10 include tissue acquisition assemblies 12 in conjunction with some or all of, for example, a support frame 58, a RF power source 38, a vacuum source 56, and a tissue collection chamber 54. These and other elements may be operably connected together with some or all of, for example, a RF cable 48 or 36, a vacuum line 52, and a ground pad 40 and ground cable 42.

A suitable source of radiofrequency energy is effective to provide radiofrequency energy of between about 35 W and about 150 W, preferably between about 50 W and about 100 W. The radiofrequency energy may suitably have a frequency of between about 0.1 MHz and about 10 MHz, preferably between about 0.3 MHz and about 1.2 MHz.

A tissue extraction tube 44 embodying features of the invention may be made with any flexible, biocompatible material. Such a tube 14 is preferably made with a flexible, non-conducting biocompatible material. Suitable materials include, but are not limited to, silicon rubber, latex and other natural and synthetic rubber materials, nylon, polyethylene block amides (such as Pebax®), thermoplastic elastomers, such as, for example, Kraton and C-Flex, and including thermoplastic polyester elastomers (e.g., Hytrel®), and other polymers, polymer blends and copolymers of polymers, including but not limited to polyacrylonitrile, polyamide, polynitrile, polyolefin, polyurethane, polyvinyl chloride, and other flexible non-conducting materials.

Tube 44 may include a strengthening filament 78 on or within its wall, shown here as a spiral coil; filament 78 may alternatively be in the configuration of a ring or rings, a braid, multiple longitudinal strips, or other configurations. A strengthening filament 78 is effective to add strength to a flexible tube, providing radial strength to prevent vacuum from causing the tube to collapse, and allowing a tube to bend without breaking or tearing. A strengthening filament may be any elongated object, such as a cord, band or other thin strip of material, and may be embedded in or attached to the tube wall. A strengthening filament may be straight, curved, coiled, ring-shaped, spiral-shaped, braided with other strengthening filaments, another shape or any combination of shapes. Strengthening filaments 78 are preferably non-conductive, and may be made from materials including, but not limited to, glass fiber, polymers such as, for example, Kevlar®, polyesters, other polymers, polymer blends and copolymers of polymers, including but not limited to polyacetal, polyacrylonitrile, polyamide, polyethylene including high density polyethylene (HDPE), polyethylene terephthalate, polyimide, poly(methyl)methacrylate, polynitrile, polyolefin, polyurethane, polypropylene, polystyrene, polysulfone, polytetrafluoroethylene (Teflon®) and other fluorinated ethylene fibers, polyvinyl chloride, and other materials such as graphite fibers. Strengthening filaments may also be made with filled materials, such as glass or mineral-filled polymers such as glass-filled polyester, mica-filled polysulfone, other filled polymers and other filled materials.

A rail 96, series of pins 97, or other tube guide embodying features of the invention may be made with a durable, biocompatible material, which is preferably non-conducting and may be flexible. Suitable materials include HDPE, polyetheylene, polyacrylonitrile, polyacetal, polyamide, polyethylene terephthalate, polyimide, poly(methyl) methacrylate, polynitrile, polyolefin, polypropylene, polystyrene, polysulfone, polytetrafluoroethylene (Teflon®) and other fluorinated ethylene polymers, polyurethane, polyvinyl chloride, Pebax®, Hytrel®, acrylonitrile-butadiene-styrene (ABS), glass- or mineral-filled polymers, such as glass-filled polyester, mica-filled polysulfone, other filled polymers and other filled materials and other biocompatible non-conducting materials. As shown in FIG. 6A, a rail may enclose a RF connection wire 102.

A shaft 14 may be made of any suitably strong biocompatible material, and preferably a non-conductive material. Thus, a shaft 14 may be made from a biocompatible polymer, composite, such as a graphite composite and an epoxy-bound braid of glass or nylon, ceramic, or other material. For example, polycarbonate is a strong and durable biocompatible material. Other suitable materials include other plastics including thermoplastics and polymers, and co-polymers, polymer alloys and polymer mixtures. Suitable materials include HDPE, polyetheylene, polyacrylonitrile, polyacetal, polyamide, polyethylene terephthalate, polyimide, poly(methyl)methacrylate, polynitrile, polyolefin, polypropylene, polystyrene, polysulfone, polytetrafluoroethylene (Teflon®) and other fluorinated ethylene polymers, polyurethane, polyvinyl chloride, Pebax®, Hytrel®, acrylonitrile-butadiene-styrene (ABS), glass- or mineral-filled polymers, such as glass-filled polyester, mica-filled polysulfone, other filled polymers and other filled materials and other biocompatible non-conducting materials. A shaft may be made from or include a metal, such as stainless steel. A metal may be coated with a ceramic, Teflon®, a polymer such as polyimide, or with any other biocompatible coating. A guide, such as a channel 106 disposed on a shaft 14, may be made of the same material as a shaft 14, may be made of a different material chosen from materials suitable for making a shaft 14, or may further include other materials or coatings. For example, a material or coating having a low coefficient of friction, such as Teflon®, may be used in the manufacture of a guide.

Rail 96 and channel 106 as shown in the Figures and described above are particular examples of guides; other guides configured to cooperate together to guide the motion of a tissue extraction tube 44 along a shaft 14 are also suitable for the practice of the invention. Thus, it will be understood that suitable guides include any elements configured to engage each other and to guide the movement of a tissue extraction tube along a tissue cutting pathway. Guides embodying features of the invention need not be continuous, unitary elements, nor need they extend along the entire length of a shaft or tube embodying features of the invention. For example, as illustrated in FIG. 5B, a guide may be a series of pins or protuberances configured and aligned so as to engage a channel. It will be understood that a shaft may have a rail, and a tube may have a channel, and that other possible configurations of guides are suitable for the practice of the invention. It will further be understood that a shaft and a tube may each, or singly, have multiple guides, such as, for example, a pair of rails configured to engage a pair of channels, or a plurality of pins aligned in a row or rows so as to fit within a slot or slots, or a multitude of parallel runners configured to engage and slide along a multitude of tracks. In further embodiments, devices embodying features of the invention may have a tube with a rail configured to move within a channel, the tube also having one or more runners configured to slide along a track or tracks.

In addition, it will be understood that in embodiments of the invention, a shaft need not have a guide. In such embodiments, a tissue extraction tube may have a guide configured to direct the movement of the flexible distal portion without engaging with another guide. Such embodiments include devices having flexible, curved guides disposed along a distal portion of a tissue extraction tube configured to direct a distal tip of the tissue extraction tube back towards a cutting bowl after the distal tip has been deflected radially out of a shaft aperture during distal movement along a shaft. Such flexible, curved guides may be ramp-shaped, and may cause the flexible distal end of a tube to assume a ramp shape as it emerges from an aperture. For example, the open distal end 76 of a tissue extraction tube 44 with a ramp-shaped curved guide on its distal portion 70 will emerge from the shaft aperture 26 as the distal portion 70 of the tube 44 moves distally and climbs up a ramp 24, enabling its loop cutter 72 to cut tissue; further distal movement of the tube 44 guided by the curved guide allows the flexible distal portion 70 to re-enter aperture 26, to enter cutting bowl 22, and to partially or completely conform to the ramp 24 when the tube 44 is extended distally along a shaft. Such flexible curved guides may be made from previously discussed materials, or other materials, such as memory materials and spring materials. Memory materials include, for example, memory metals such as nickel titanium alloys, and spring materials include plastic spring materials and metal spring material, such as, for example, spring steel.

Aperture 26 is illustrated in the Figures as an uncovered opening through the wall of shaft 14. In some embodiments of the devices of the invention, aperture 26 is covered by a movable aperture cover. In some methods of collecting tissue samples embodying features of the invention, an aperture cover is in place over an aperture 26 during placement or removal of shaft 14 at or from a desired location within a patient's body, and the cover is moved during collection of a tissue sample so as to expose aperture 26.

Preferably, the systems, assemblies and devices embodying features of the invention are made from materials that are suitable for sterilization, including ultraviolet, chemical and radiation sterilization. Such sterilizable materials include metals, glasses, ceramics, composites, plastics, thermoplastics and thermoplastic elastomers, and other polymers including, but not limited to polyethylene, HDPE, Kevlar®, C-Flex, polypropylene, polyacrylonitrile, polyamide, polyethylene terephthalate, polyimide, poly(methyl) methacrylate, polynitrile, polyolefin, polypropylene, polystyrene, polysulfone, polytetrafluoroethylene (Teflon®) and other fluorinated ethylene polymers, polyurethane, polyvinyl chloride, and other biocompatible non-conducting materials and other materials.

Assemblies, devices and systems embodying features of the invention may be used to cut and to collect tissue samples from within a patient's body. A skin incision is typically needed to access a body location to obtain a tissue sample. Skin incisions are often made using scalpels or other sharp cutting tools, although RF cutters may also be used. A distal cutter 20 may be used to make an initial skin incision, or, alternatively, another cutting instrument maybe used to cut through a patient's skin. A distal cutter 20 is effective to cut through body tissue below the skin to provide a path for the insertion of a shaft 14 into a desired location within a patient's body. Methods for removing a tissue specimen from within a body include placing a shaft 14 adjacent a tissue mass of interest located within a patient's body. A hollow tube 44 may be in place within the shaft 14 during insertion of a shaft 14 into a patient's body, or may be placed within the shaft after the shaft is inserted into a patient's body. Advancing the hollow tube 14 along ramp guide 24 out of a shaft aperture 26 exposes tissue to loop cutter 72, which is effective to cut tissue surrounding the shaft. Where loop cutter 72 is a RF cutter, loop cutter 72 is activated with RF energy during advancement outside of the aperture 26. Distal advancement of the loop cutter 72 disposed about orifice 76 is effective to cut a swath of tissue, which may be sucked into orifice 76 by vacuum applied via tube bore 92 originating from a vacuum source 56. Further distal advancement of loop cutter 72 brings it back into the shaft aperture 26; this movement, by bringing loop cutter 72 past aperture edge 27, is effective to cut any tissue still connecting the tissue swath with the tissue bed. The completely severed tissue sample within tube bore 92 is drawn by vacuum proximally along the length of tube 44, through vacuum line 52 and into tissue collection chamber 54.

Thus, one tissue sampling method embodying features of the invention includes placing a shaft 14 adjacent a tissue mass within a body; advancing a tissue extraction tube 44 with a flexible distal portion 70 and a distal cutting element 72 through the shaft bore 110 so that distal cutting element 72 and distal portion 70 advance at least partially out of aperture 26 and advance through tissue, cutting a tissue sample. Preferably, cutting element 72 is a RF cutter, and RF power is applied to cutting element 72 as it advances, effective to cut tissue. Application of vacuum draws surrounding tissue towards hollow tube 44, where it may be cut by the advancing cutting element 72, providing a tissue sample. The above method, where shaft 14 has a guide such as a channel 106 and tube 44 has a guide such as a rail 96, may further include guiding the tube 44 by engaging the rail 96 with the channel 106. Methods embodying features of the invention may also include guiding a hollow tube 44 out of an aperture 26 while the tube 44 travels over a ramp guide 24. Methods further include activating an RF cutter 72 to cut tissue, and cutting tissue while a hollow tube 44 is guided out of an aperture 26 while the tube 44 travels over the ramp guide 24. Applying vacuum to a proximal part 43 of a hollow tube 44 is effective to transport a tissue specimen proximally to a tissue collection chamber 54.

Tissue collection methods also include collection of multiple tissue samples. Multiple tissue samples may be collected from one location or from multiple locations using methods of the present invention. A method for collecting multiple tissue samples includes placing a shaft 14 adjacent tissue; advancing a tissue extraction tube 44 in a distal direction so that its distal end 70 and distal cutter 72 advance through tissue for a first time; cutting a first tissue sample; advancing a tissue extraction tube 44 in a distal direction so that its distal end 70 and distal cutter 72 advance through tissue for a second time; and cutting a second tissue sample. In preferred methods of collecting multiple samples, distal cutter 72 is a RF cutter and RF power is supplied to distal cutter 72 while tissue samples are taken. Distal end 70 and distal cutter 72 may be retracted in a proximal direction back within bore 110 between sample acquisitions. Preferred methods of collecting multiple samples include rotating the shaft 14 and tube 44 around a longitudinal axis 80, preferably between collection of a first and a second sample. Such rotation may be accomplished by turning a thumbwheel, preferably to preset locations designated by detents or indentations. Alternatively, a shaft 14 and tube 44 may be rotated by an arbitrary amount. Rotational force may be applied manually, for example, by an operator's hand rotating a thumbwheel 32, or by mechanical, electrical, or other means of providing rotational force.

An advantage of this method is that multiple samples may be obtained from a single shaft position by rotating the shaft around a longitudinal axis while it remains inserted within a patient's body. Thus, multiple samples may be recovered from different positions oriented at designated radial positions around an initial biopsy site. In addition, the positions may be known and recorded by clinical operators, so that the locations from which samples were taken may be known. A shaft 14 may be moved in a longitudinal direction between sample acquisitions, as well as, or instead of, rotating the shaft between sample acquisitions.

It will be apparent from the foregoing that, while particular forms of the invention have been illustrated and described herein primarily in terms of an electrosurgical specimen-collection system, various modifications can be made without departing from the spirit and scope of the invention. Moreover, those skilled in the art will recognize that features shown in one embodiment may be utilized in other embodiments. Terms such a "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action.

While particular forms of the invention have been illustrated and described, it should be apparent that various modifications can be made without departing from the spirit and scope of the invention. Accordingly, it is not intended that the invention be limited, except as by the appended claims.

What is claimed is:

1. A tissue extraction device comprising:
   an elongated shaft having a proximal portion, a distal portion with a distal tip having a tissue penetrating element, an inner bore, an aperture on said shaft distal portion in fluid communication with said bore, and a guide extending along said distal portion to define a tissue cutting pathway; and
   a tissue extraction member which is movably disposed at least in part within said shaft inner bore, which has an elongated hollow tube having a proximal tubular portion, a flexible distal tubular portion, a longitudinal bore in the flexible distal tubular portion, a distal end, a tissue receiving port in fluid communication with the bore and a tissue cutting surface at the distal end, and a guide follower on the distal tubular portion configured to engage the guide on the elongated shaft so as to direct movement of the flexible distal tubular portion along the tissue cutting pathway.

2. The tissue extraction device of claim 1, wherein said longitudinal bore extends through said elongated hollow tube, and the proximal tubular portion is configured to operably connect with a vacuum source.

3. The tissue extraction device of claim 1, wherein said tissue cutting surface is a radiofrequency cutting element.

4. The tissue extraction device of claim 1, wherein the tissue penetrating element a radiofrequency cutting element.

5. The tissue extraction device of claim 4, wherein the radiofrequency cutting element is spaced distally away from the distal tip.

6. The tissue extraction device of claim 5, wherein the radiofrequency cutting element comprises a plurality of cutting wires.

7. The tissue extraction device of claim 6, wherein said plurality of cutting wires comprises a pair of cutting wires each having a portion extending from the distal tip to a distance greater than a width of the distal tip.

8. The tissue extraction device of claim 7, wherein said pair of cutting wires extends away from the distal tip along radial directions separated by about 180°.

9. The tissue extraction device of claim 5, wherein at least a portion of radiofrequency cutting element extends away from the distal tip to a distance greater than a width of the distal tip.

10. The tissue extraction device of claim 1, wherein the guide defines at least in part a non-axial pathway.

11. The tissue extraction device of claim 10, wherein the shaft further has a plurality of radial positions and a non-axial ramp surface on said inner bore within said distal portion of said shaft, said guide being disposed on said non-axial ramp surface, said aperture being located along said distal portion of said shaft so that at least a portion of said non-axial ramp surface extends substantially towards said aperture.

12. The tissue extraction device of claim 11, said ramp surface having a distal portion, said shaft further comprising a chamber disposed adjacent a distal portion of said ramp surface, accessible from said aperture, and configured to receive at least a portion of the distal end of said tissue extraction member.

13. The tissue extraction device of claim 10, further comprising a vacuum vent disposed on said shaft distal portion.

14. The tissue extraction device of claim 1, further comprising a vacuum vent disposed on said shaft distal portion.

15. A biopsy device for cutting tissue, comprising:
   a. an elongated shaft which has a longitudinal axis, a proximal shaft portion, a distal shaft portion with a distal tip having a tissue penetrating element, an inner bore, an aperture on the distal shaft portion in fluid communication with said bore and a guide on the distal shaft portion defining a non-axial tissue cutting pathway; and
   b. an elongated cutting member which is at least in part movably disposed within the bore of the elongated shaft and which has a proximal portion, a flexible distal portion, a tissue cutting member on the distal open end, a guide follower on the flexible distal portion configured to direct movement of the tissue cutting member along the tissue cutting pathway to cut tissue disposed about said shaft.

16. A method for obtaining a tissue sample from a target site within a patient's body, comprising:
   a) providing a biopsy device having an elongated shaft with a guideway defining an arcuate tissue cutting pathway which extends away from a longitudinal axis of the elongated shaft and toward the longitudinal axis and having an elongated tissue cutting member with a guide following element which engages the guideway so as to follow the pathway when cutting a tissue sample;
   b) placing the biopsy device adjacent a tissue mass within the patient's body; and
   c) advancing the elongated tissue cutting member along the arcuate tissue cutting pathway to cut a tissue sample from the target site within the patient's body.

17. The method of claim 16, wherein cutting a tissue sample comprises cutting a tissue sample with a radiofrequency cutting element.

18. The method of claim 16, further comprising applying vacuum within the biopsy device effective to draw tissue towards said cutting member.

19. The method of claim 18, further comprising applying vacuum effective to draw tissue into said shaft.

20. The method of claim 16, wherein the guideway defining a tissue cutting pathway has a ramp which extends away from a longitudinal axis of the elongated shaft, and wherein the ramp guides a distal cutting element out of an aperture in the shaft while said elongated cutting member travels over said ramp.

21. The method of claim 20, wherein said shaft has a distal cutting bowl, wherein said distal movement is effective to guide a distal cutting element on said elongated cutting member out of said aperture and into said cutting bowl.

22. The method of claim 21, further comprising applying vacuum effective to draw tissue towards said cutting member.

23. The method of claim 22, further comprising applying vacuum effective to draw tissue towards said cutting bowl.

24. A method for obtaining multiple tissue samples from a target tissue mass within a patient's body, comprising:
   a) providing a tissue collection system having an elongated shaft with a bore extending therein and with a guideway defining a tissue cutting passageway that extends radially away from a longitudinal axis of the elongated shaft and having an elongated tissue cutting member which has a cutting element on a flexible distal portion on the tissue cutting member, which is disposed at least in part within the bore of the elongated shaft and which has a follower that engages the guideway so as to follow the tissue cutting passageway when cutting a tissue sample;
   b) disposing a distal portion of the elongated shaft of the tissue collection system adjacent the target tissue mass within the patient's body;
   c) advancing the elongated tissue cutting member within said bore in a distal direction, said elongated cutting member having a distal cutting element on a flexible distal portion extending out of the bore configured to follow a non-axial tissue cutting pathway;
   to cut a first tissue sample;
   withdrawing the tissue cutting member at least in part back into the bore;
   rotating the elongated shaft to change the location of the tissue cutting pathway; and
   advancing the flexible distal portion of the elongated tissue cutting member out of the bore to follow the non-axial tissue cutting pathway to cut a second tissue sample.

25. The method for obtaining multiple tissue samples from within a body of claim 24, wherein cutting a tissue sample comprises cutting a tissue sample with a radiofrequency cutting element.

26. The method for obtaining multiple tissue samples from within a body of claim 24, further comprising rotating said shaft around a longitudinal axis.

27. The method for obtaining multiple tissue samples from within a body of claim 26, further comprising retracting in a proximal direction said elongated cutting member into said bore effective that said distal cutting element is not substantially disposed out of said aperture.

28. The method for obtaining multiple tissue samples from within a body of claim 24, further comprising retracting in a proximal direction said elongated cutting member into said bore effective that said distal cutting element is not substantially disposed out of said aperture.

29. The method of claim 24, further comprising applying vacuum effective to draw tissue towards said cutting element.

30. The method of claim 29, wherein said shaft has a distal cutting bowl, wherein said distal movement is effective to guide said distal cutting element and said elongated cutting member out of an aperture in said shaft and into said cutting bowl.

31. The method of claim 30, further comprising applying vacuum effective to draw tissue towards said cutting bowl.

32. The method of claim 24, further comprising applying vacuum effective to draw tissue towards said shaft.

33. The method of claim 32, further comprising applying vacuum effective to draw tissue towards said cutting element.

34. The method of claim 24, wherein said shaft comprises a first guide and said elongated cutting member comprises a second guide, further comprising engaging said guides effective to guide said cutting element.

35. The method of claim 24, wherein said bore comprises a ramp, further comprising guiding said distal cutting element out of an aperture in said shaft while said elongated cutting member travels over said ramp.

36. A biopsy device, comprising:
   a. an elongated shaft having a proximal shaft section, a distal shaft section, an inner bore, and a guide means extending within the distal shaft section for defining a tissue cutting pathway; and b. an elongated tissue cutting member which is at least in part movably disposed within the bore of the elongated shaft and which has a proximal portion, a flexible distal portion with a distal open end, a tissue cutting means disposed on the distal open end, a follower means on the flexible distal portion for engaging the guide means and for facilitating movement of the tissue cutting means on the distal open end of the flexible distal portion along the tissue cutting pathway defined by the guide means in the distal shaft section of the elongated shaft.

37. A tissue extraction device comprising:

an elongated shaft having a proximal portion, a distal portion with a distal tip having a shaft cutting means, an inner bore, an aperture on said shaft distal portion connected with said bore, and a guide means extending along said distal portion for defining a tissue cutting pathway; and a tissue extraction member movably disposed at least in part within said shaft inner bore, comprising an elongated hollow tube having a tube proximal portion, a flexible tube distal portion, a tube distal end having a longitudinal bore connecting with a tissue receiving port with a rim, a tissue cutting means disposed about at least a portion of said rim, and a follower configured to engage said guide means to follow the tissue cutting pathway defined thereby.

* * * * *

UNITED STATES PATENT AND TRADEMARK OFFICE
CERTIFICATE OF CORRECTION

PATENT NO. : 6,875,182 B2  Page 1 of 1
DATED : April 5, 2005
INVENTOR(S) : Wardle et al.

It is certified that error appears in the above-identified patent and that said Letters Patent is hereby corrected as shown below:

<u>Title page,</u>
Item [63], Related U.S. Application Data, after "now Pat. No. 6,331,166", insert -- which claims benefit of provisional application 60/076,093, filed March 3, 1998, --.

Signed and Sealed this

Twenty-third Day of May, 2006

JON W. DUDAS
*Director of the United States Patent and Trademark Office*